United States Patent [19]

Riondel

[11] Patent Number: 5,719,314
[45] Date of Patent: Feb. 17, 1998

[54] PROCESS FOR THE PREPARATION OF ISOBORNYL (METH)ACRYLATE

[75] Inventor: Alain Riondel, Forbach, France

[73] Assignee: Elf Atochem S.A., Puteaux, France

[21] Appl. No.: 698,995

[22] Filed: Aug. 16, 1996

[30] Foreign Application Priority Data

Aug. 18, 1995 [FR] France ................... 95-09916

[51] Int. Cl.$^6$ ............................ C07C 69/52
[52] U.S. Cl. .................................. 560/220
[58] Field of Search ........................... 560/220

[56] References Cited

U.S. PATENT DOCUMENTS 5,399,744   3/1995   Pfirmann et al. ............ 560/231

FOREIGN PATENT DOCUMENTS 677506   10/1995   European Pat. Off. .

*Primary Examiner*—Paul J. Killos
*Attorney, Agent, or Firm*—Millen, White, Zelane, & Branigan, P.C.

[57] ABSTRACT

This process for the preparation of isobornyl (meth)acrylate comprises the reaction of (meth)acrylic acid with camphene in the presence of a solid zirconium-based superacid as catalyst.

8 Claims, No Drawings

PROCESS FOR THE PREPARATION OF ISOBORNYL (METH)ACRYLATE

BACKGROUND OF THE INVENTION

The present invention relates to a process for the preparation of isobornyl methacrylate and of isobornyl acrylate.

U.S. Pat. No. 3,087,962 provides a process for the preparation of isobornyl acrylate or methacrylate by reaction of acrylic or methacrylic acid with camphene, it being observed that a rearrangement then takes place. The process is carried out in the presence of a strong acid catalyst, such as sulphuric acid, or a Lewis acid, such as boron trifluoride. This process cannot be used on an industrial scale, due to its low yield and to the corrosion of reactors caused by the boron trifluoride.

To overcome this, the Japanese patent application published under No. 58 049 337 provides a process for the preparation of isobornyl acrylate and methacrylate of the same type as that mentioned above but in which the reaction is catalysed by a strong sulphonic cationic resin. Side reactions take place which have their origin mainly in the dimerization of camphene to diterpene, which has an effect on the selectivity of the reaction.

SUMMARY OF THE INVENTION

The invention overcomes these disadvantages by using a catalyst which gives a selectivity towards isobornyl acrylate and methacrylate which is better than any known catalyst and which represents the best compromise between yield and selectivity towards ester.

The subject of the invention is therefore a process for the preparation of isobornyl acrylate and methacrylate of formula

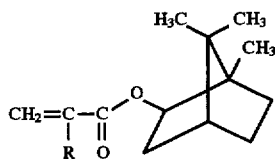

in which R is a hydrogen atom or methyl radical, by reaction of acrylic or methacrylic acid of formula

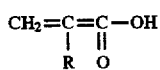

with camphene of formula

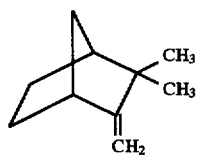

in the presence of a catalytic amount of an acid catalyst, characterized in that it comprises the use, as the catalyst, of a solid zirconium-based superacid.

The molar ratio of the acid to camphene can be between 4/1 and 1/4 and preferably between 2/1 and 1/2.

The reaction temperature is between 10° and 60° C. and preferably between 30° and 40° C.

The reaction time can be between 2 and 10 hours.

The use of solvents, such as cyclohexane, hexane or toluene, is possible.

It is recommended to use, under air bubbling, inhibitors such as hydroquinone, the monomethyl ether of hydroquinone, phenols substituted by highly sterically hindering alkyl groups or phenothiazine, in an amount of between 150 and 3000 ppm with respect to the acid.

Use may in particular be made of a catalyst, in an amount of between 2 and 20% by weight with respect to the total charge and preferably of 5 to 15%, which catalyst is a product from the reaction of zirconium hydroxide with ammonium sulphate, which may be prepared in the following way:

I—Preparation of $Zr(OH)_4$ 88 g of $ZrOCl_2$ octahydrate are dissolved at room temperature in 800 ml of water in a 1-liter jacketed reactor equipped with:

a stirrer a temperature probe a pH probe.

Approximately 50 ml of 25% $NH_4OH$ are introduced slowly, still at room temperature, so that the pH of the final solution is between 8 and 9.

The white $Zr(OH)_4$ precipitate obtained is then:

1) washed with water to remove the chloride ions 2) dried in an oven at 100° C. under reduced pressure overnight.

Approximately 40 g of dry $Zr(OH)_4$ are thus obtained.

II—Sulphation/Calcination $Zr(OH)_4$ and $NH_4(SO_4)_2$ (15% by weight/$Zr(OH)_4$) are mixed using a mill.

The solid obtained is then calcined under dry air at 650° C.

After cooling, a white solid is obtained which is denoted by ZrSA15.

EXAMPLES

Example 1

Preparation of Isobornyl Methacrylate (ISOBORMA)

The ZrSA15 catalyst (20.5 g); the methyl ether of hydroquinone (0.018 g) and part of the methacrylic acid (49.5 g) are introduced into a 250-ml jacketed glass reactor equipped with a temperature probe. The combined reactor and contents are brought, while bubbling with air, to 35° C. and the camphene (136 g), dissolved in the remaining methacrylic acid (43.8 g), is introduced into the mixture over 1.5 h. The mixture is then kept stirring for 4.5 hours. At the end of the reaction, a sample of the crude reaction mixture is analysed by:

potentiometry gas phase chromatography in order to determine the conversion of the camphene, the isobornyl methacrylate/camphene yield and the isobornyl methacrylate/camphene selectivity.

The results obtained are collated in Table 1.

Example 2

(Comparative)

Example 1 is repeated, apart from replacing the catalyst by Amberlyst 15 (A15), an acid resin containing sulpho groups.

The results obtained are recorded in Table 1:

TABLE 1

| Synthesis of ISOBORMA Results | | |
|---|---|---|
| C (%) Camphene conversion | Y (%) of ISOBORMA | S (%) Selectivity towards ISOBORMA |
| Example 1 74.14 | 73.4 | 98.9 |
| Example 2 86 | 75 | 87.2 |

In Example 2, the conversion is better but there are more by-products.

It emerges from these tests that the best yield/selectivity compromise is obtained by using ZrSA15.

Example 3

Preparation of Isobornyl Acrylate (ISOBORA)

The operating conditions of Example 1 are repeated, apart from replacing methacrylic acid with acrylic acid. The amount of acrylic acid used is 75.5 g, of which 47.5 g are introduced into the reactor from the start. At the end of the reaction, a sample of the crude reaction mixture is analysed in the same way as during Example 1, in order to determine the conversion of the camphene, the isobornyl acrylate/camphene yield and the isobornyl acrylate/camphene selectivity. The results obtained are given in Table 2.

Example 4

Example 3 is repeated, apart from replacing the catalyst by Amberlyst 15 (A15), an acid resin containing sulpho groups.

The results obtained are reported in Table 2.

TABLE 2

| Synthesis of ISOBORA Results | | |
|---|---|---|
| Conversion of the camphene (%) | ISOBORA yield (%) | ISOBORA selectivity (%) |
| Example 3 75.1 | 73.8 | 98.2 |
| Example 4 88.2 | 84.7 | 96.2 |

As regards selectivity, it is observed that ZrSA15 is substantially better than A15.

I claim:

1. A process for the preparation of isobornyl (meth)-acrylate of formula

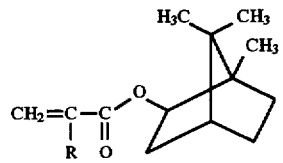

in which R is a hydrogen atom or a methyl radical, comprising reacting (meth)acrylic acid of formula

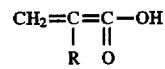

with camphene of formula

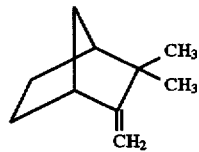

in the presence of a catalytic amount of an acid catalyst which comprises a solid zirconium-based superacid.

2. A process according to claim 1, wherein the catalyst is a product of the reaction of zirconium hydroxide with ammonium sulphate.

3. A process according to claim 1, wherein the molar ratio of the acid to camphene is 4/1 to 1/4.

4. A process according to claim 1, comprising bringing the mixture into contact with the catalyst at a temperature of 10° to 60° C.

5. A process according to claim 3, wherein the molar ratio of acid to camphene is 2/1 to 1/2.

6. A process according to claim 4, wherein the temperature is 30°–40° C.

7. A process according to claim 1, wherein the reaction is conducted under bubbling of air, in the presence of an inhibitor.

8. A process according to claim 7, wherein the inhibitor is hydroquinone, a phenol substituted by a sterically hindering alkyl group, or phenothiazine.

* * * * *